(12) United States Patent
Madjarov et al.

(10) Patent No.: US 12,324,912 B2
(45) Date of Patent: Jun. 10, 2025

(54) DEVICES, SYSTEMS, AND METHODS FOR TREATING CARDIAC ARRHYTHMIAS

(71) Applicant: Atrium Health, Charlotte, NC (US)

(72) Inventors: Jeko Metodiev Madjarov, Charlotte, NC (US); Svetozar Madzharov, Sofia (BG)

(73) Assignee: ATRIUM HEALTH, Charlotte, NC (US)

( * ) Notice: Subject to any disclaimer, the term of this patent is extended or adjusted under 35 U.S.C. 154(b) by 0 days.

(21) Appl. No.: 16/342,904

(22) PCT Filed: Oct. 16, 2017

(86) PCT No.: PCT/US2017/056768
§ 371 (c)(1),
(2) Date: Apr. 17, 2019

(87) PCT Pub. No.: WO2018/075396
PCT Pub. Date: Apr. 26, 2018

(65) Prior Publication Data
US 2019/0240481 A1 Aug. 8, 2019

Related U.S. Application Data

(60) Provisional application No. 62/408,994, filed on Oct. 17, 2016.

(51) Int. Cl.
*A61N 1/00* (2006.01)
*A61B 5/00* (2006.01)
(Continued)

(52) U.S. Cl.
CPC .......... *A61N 1/0573* (2013.01); *A61B 5/0006* (2013.01); *A61B 5/29* (2021.01);
(Continued)

(58) Field of Classification Search
CPC .... A61N 1/0573; A61N 1/3756; A61N 1/368; A61N 1/0563; A61N 1/39622;
(Continued)

(56) References Cited

U.S. PATENT DOCUMENTS 4,030,509 A 6/1977 Heilman et al.
4,169,479 A * 10/1979 Muto .................... A61N 1/0565
607/9
(Continued)

FOREIGN PATENT DOCUMENTS

WO WO2016/038599 A1 * 3/2016 ......... A61N 1/36542

OTHER PUBLICATIONS

International Search Report and Written Opinion corresponding to PCT/US2017/056768, mailed Jan. 2, 2018, 10 pages.
(Continued)

*Primary Examiner* — Scott M. Getzow
(74) *Attorney, Agent, or Firm* — J. Clinton Wimbish; Maynard Nexsen PC (57) ABSTRACT

Devices, systems, and methods for treating cardiac arrhythmias are disclosed. An exemplary device includes a support member having a first end and a second. At least a first pacing electrode is located proximate the first end of the support member and at least a second pacing electrode is located proximate the second end of the support member. A defibrillating electrode is located between the first pacing electrode and the second pacing electrode. An exemplary method of treating a patient comprises a device for treating cardiac arrhythmias and placing the device adjacent a heart of the patient.

18 Claims, 2 Drawing Sheets

(51) Int. Cl.
  *A61B 5/29*    (2021.01)
  *A61N 1/05*    (2006.01)
  *A61N 1/368*   (2006.01)
  *A61N 1/375*   (2006.01)
  *A61B 17/00*   (2006.01)
  *A61N 1/372*   (2006.01)
  *A61N 1/39*    (2006.01)

(52) U.S. Cl.
  CPC ........... *A61N 1/0563* (2013.01); *A61N 1/368* (2013.01); *A61N 1/3756* (2013.01); *A61B 2017/00867* (2013.01); *A61B 2560/0214* (2013.01); *A61B 2562/043* (2013.01); *A61N 1/37205* (2013.01); *A61N 1/37211* (2013.01); *A61N 1/37518* (2017.08); *A61N 1/39622* (2017.08)

(58) Field of Classification Search
  CPC ........... A61N 1/37205; A61N 1/37518; A61N 1/3721; A61N 1/37211; A61B 5/0006; A61B 5/042; A61B 2017/00867; A61B 2562/043; A61B 2560/0214; A61B 5/29; A61B 5/283
  See application file for complete search history.

(56) References Cited

U.S. PATENT DOCUMENTS

| | | | | |
|---|---|---|---|---|
| 5,368,592 | A * | 11/1994 | Stern | A61M 25/0147 403/90 |
| 5,456,706 | A | 10/1995 | Pless et al. | |
| 5,683,447 | A * | 11/1997 | Bush | A61N 1/056 607/126 |
| 6,083,216 | A * | 7/2000 | Fischer, Sr. | A61N 1/056 600/374 |
| 7,010,358 | B1 * | 3/2006 | Kroll | A61N 1/0563 607/122 |
| 7,363,082 | B2 * | 4/2008 | Ransbury | A61N 1/37512 607/36 |
| 7,389,134 | B1 * | 6/2008 | Karicherla | A61B 5/0215 600/375 |
| 7,684,864 | B2 * | 3/2010 | Olson | A61N 1/37518 607/36 |
| 7,856,260 | B1 * | 12/2010 | Ryu | A61N 1/0587 600/374 |
| 2002/0103507 | A1 * | 8/2002 | Helland | A61N 1/3918 607/5 |
| 2004/0147994 | A1 | 7/2004 | Zhang et al. | |
| 2005/0010095 | A1 | 1/2005 | Stewart et al. | |
| 2005/0288666 | A1 * | 12/2005 | Bertolero | A61B 18/14 606/41 |
| 2007/0038279 | A1 * | 2/2007 | Fifer | A61N 1/056 607/116 |
| 2008/0140139 | A1 | 6/2008 | Heinrich et al. | |
| 2009/0192555 | A1 * | 7/2009 | Schleicher | A61N 1/37518 607/2 |
| 2009/0210044 | A1 * | 8/2009 | Reddy | A61N 1/056 607/122 |
| 2010/0171394 | A1 * | 7/2010 | Glenn | H02N 2/18 310/339 |
| 2011/0112597 | A1 * | 5/2011 | Snell | A61B 5/0452 607/27 |
| 2013/0073029 | A1 * | 3/2013 | Shaw | A61B 17/12122 623/1.36 |
| 2013/0184799 | A1 * | 7/2013 | Kipke | A61N 1/0551 607/118 |
| 2014/0330327 | A1 * | 11/2014 | Thompson-Nauman | A61N 1/05 607/119 |
| 2015/0045784 | A1 * | 2/2015 | Kunis | A61F 2/89 606/30 |
| 2015/0202437 | A1 * | 7/2015 | Franke | A61B 18/1206 607/42 |
| 2016/0015394 | A1 | 1/2016 | Cedro, Jr. et al. | |
| 2016/0158545 | A1 * | 6/2016 | Khairkhahan | A61N 1/368 607/19 |
| 2016/0228712 | A1 * | 8/2016 | Koop | A61N 1/368 |
| 2017/0312494 | A1 * | 11/2017 | Seifert | A61N 1/05 |
| 2018/0126152 | A1 * | 5/2018 | Leven | A61N 1/0551 |
| 2018/0263688 | A1 * | 9/2018 | Barrish | A61B 5/6853 |

OTHER PUBLICATIONS

Office Action issued in Chinese Application No. 201780064124.8 dated Jun. 29, 202;pp. 1-11.

* cited by examiner

DEVICES, SYSTEMS, AND METHODS FOR TREATING CARDIAC ARRHYTHMIAS

CROSS-REFERENCE TO RELATED APPLICATIONS

This application is a U.S. National Phase of PCT/US2017/056768, filed Oct. 16, 2017, which claims priority pursuant to 35 U.S.C. § 119 to U.S. Provisional Application No. 62/408,994 filed Oct. 17, 2016, each of which is incorporated by reference herein in its their entireties.

FIELD

This application relates generally to devices, systems, and methods of treating heart disorders and, more particularly, to devices, systems, and methods for treating cardiac arrhythmias via pacing and/or defibrillating procedures.

BACKGROUND

As the heart is a vital organ in the human body, it is essential to ensure that it functions properly. Proper functioning relies, in part, upon the synchronized contraction of the muscle tissue in the heart at regular intervals. In healthy hearts, electrical impulses generated by the sinoatrial node propagate to different areas of the heart and stimulate respective areas of muscle tissue, causing the left and right atria of the heart to contract first, followed by contraction of the left and right ventricles. This pattern of contraction continues and generates a series of heartbeats. Controlled stimulation of the heart muscle provides efficient contraction of all four chambers of the heart, which allows life-sustaining blood to pump through the lungs and circulatory system.

Heart disorders, including cardiac arrhythmias, can occur when the electrical impulses in the heart misfire and cause the heart to contract abnormally, for example, and beat too quickly, too slowly, or irregularly. Most arrhythmias are considered harmless and left untreated, however; other arrhythmias are extremely dangerous and require treatment and/or management. For example, arrhythmias caused by damaged heart tissue, coronary heart disease, coronary artery disease, high blood pressure, diabetes, and hyperthyroidism, among other causes, can be dangerous and result in collapse, cardiac arrest, or sudden death if left untreated.

In cases where an arrhythmia is caused by damaged heart tissue, the damage may be located in one or more layers of the heart's cardiac wall. Accordingly, there is a need for devices, systems, and methods for treating cardiac arrhythmias in any or all layers of the cardiac wall in a manner that is safe, reproducible, simple to administer, effective, efficient, adaptable to various patients (e.g., children, adults, etc.), minimally invasive, and allows for faster recovery of the patient.

SUMMARY

Devices, systems, and methods for treating cardiac arrhythmias are described herein. Such devices, systems, and methods, in some cases, can provide one or more advantages compared to previous devices and methods. For example, in some instances, devices herein are at least partially flexible and/or deformable, allowing the device to more closely conform to contours of the heart and more precisely map and/or electrically stimulate targeted tissue. Additionally, the devices, systems, and methods described herein can perform mapping, pacing, and/or defibrillating procedures on one or more layers of the cardiac wall via an epicardial or extra-pericardial approach in a minimally invasive (e.g., orthoscopic) surgical procedure.

In one aspect, devices for treating cardiac arrhythmias are provided. Such devices can comprise a support member comprising a first end and a second end opposing the first end. A plurality of pacing electrodes can be supported on or over the support member. At least a first pacing electrode can be disposed proximate the first end of the support member and at least a second pacing electrode can be disposed proximate the second end of the support member. At least one defibrillating electrode can be disposed between the first pacing electrode and the second pacing electrode.

In some embodiments, the support member comprises a central portion defining a longitudinal axis. The central portion is disposed between the first and second ends of the support member, and at least one of the first and second ends is configured to flex or bend relative to the longitudinal axis. In certain embodiments, each of the first and second ends is configured to flex or bend relative to the longitudinal axis.

Additionally, the support member can comprise at least a first joint connecting the first end to the central portion and at least a second joint connecting the second end to the central portion.

Notably, the support member can be positionable between a linear configuration and at least one non-linear configuration, such that the first end of the support member contours a first region of the heart and the second end of the support member contours a second region of the heart. The support member of devices described herein can readily conform to any size, shape, and/or curvature of a respective patient's heart.

In some embodiments, the defibrillating electrode comprises a coil that is wrapped on or over portions of the support member. In further embodiments, the pacing electrodes can be configured and used as mapping electrodes configured to map damaged areas of the heart during a mapping procedure. The mapping/pacing electrodes can be disposed along an entire length of the support member, portions of the entire length, or confined to the first and second ends, as needed.

Devices for treating cardiac arrhythmias as described herein can further comprise an attachment member disposed at the first and/or the second end of the support member for attaching the device to a portion of the heart. The device may be attached to the pericardium or a surface of the pericardium (e.g., the epicardium) during a minimally invasive (e.g., orthoscopic) surgical procedure.

Further, a plurality of anchor members can be provided for anchoring the device to the heart and in a respective position relative to the heart. In some embodiments, the anchor members can extend and retract relative to a surface of the support member and are operable, in an extended position, to engage a portion of the heart to inhibit movement of the device in a distal and/or proximal direction. In some embodiments, the anchor members are acutely or obtusely angled relative to the surface of the support member.

Devices for treating cardiac arrhythmias can further comprise a plurality of distal anchor members disposed at the first end of the support member to inhibit movement of the device in the distal direction and a plurality of proximal anchor members disposed at the second end of the support member to inhibit movement of the device in the proximal direction. A plurality of anchor members can be disposed at each of the first end, the second end, and the central portion of the support member, where desired, for inhibiting movement of the device relative to the heart.

Additionally, the support member can comprise a hollow tube. The first end of the support member can be a free end of the tube, which is not connected to an electrical lead, wire, or connector. The second end of the support member can be attached to a pulse generator. The pulse generator can supply electrical current to one or more pacing electrodes and/or the defibrillating electrode. An electrical bias can be established across one or more of the electrodes and transmit electrical energy to one or more target areas of the heart during a pacing or defibrillating procedure to regulate a pattern of heartbeats and/or generate a heartbeat.

In some embodiments, a plurality of electrical connectors (e.g., leads, wires, etc.) can connect the pulse generator to one or more of the plurality of mapping/pacing/defibrillating electrodes, and electrically communicate to one or more of the respective electrodes. In some embodiments, the plurality of electrical connectors is housed within a portion of the support member.

In another aspect, a method of treating a patient is described herein. The method comprises providing a device for treating cardiac arrhythmias as described herein. The device can include any or all of the features described hereinabove. The method of treating the patient further comprises disposing the device adjacent a heart of the patient.

In some embodiments, disposing the device adjacent the heart of the patient comprises making an incision in a thoracic area of the patient's body and inserting the device into the incision.

In further embodiments, inserting the device into the incision comprises inserting the entire device into the incision such that no portion of the device is disposed outside of the patient's body. In certain embodiments, inserting the device into the incision comprises inserting only a portion of device into the incision such that at least some portion of the device remains outside of the patient's body.

Further, disposing the device adjacent the heart of the patient further can comprise flexing the first end of the support member relative to the longitudinal axis defined by the central portion of the support member for positioning the first pacing electrode proximate a first region of the heart and flexing the second end of the support member relative to the longitudinal axis for positioning the second pacing electrode proximate a second region of the heart.

Methods described herein can further comprise attaching the first end of the support member to a first region of the heart via an attachment member and/or anchoring the device in a first position relative to the heart using one or more anchoring members extending from a surface of the device.

In further embodiments, the method of treating a patient comprises energizing one or more of the plurality of pacing electrodes with electrical energy and transmitting the electrical energy to the heart during a pacing or defibrillating operation.

Moreover, methods described herein can further comprise disposing an antimicrobial coating, cuff, or envelope around portions of the device for minimizing the potential for infection during treatment with the device.

Further, in some embodiments methods of treating a patient described herein further comprise removing the device from the patient's body after a predetermined period of time, the predetermined period of time ranging from about one hour to about fourteen days. In other embodiments, methods of treating a patient described herein further comprise retaining the device within the patient's body for a period of time ranging from about one year to about twenty years.

Methods described herein can further comprise coupling the device to a data recorder that records heart-related data. The heart-related data collected via the data recorder can be transmitted and/or read through the patient's skin. In some embodiments, the heart-related data is downloaded to a computer via a wireless connection, a wired connection, or the Internet.

These and other embodiments are described in more detail in the detailed description that follows.

DETAILED DESCRIPTION

Devices, systems, and methods of treating cardiac arrhythmias are described herein. Notably, the devices, systems, and methods set forth herein improve the ability to selectively deliver one or more targeted electrical pulses to a patient's heart, as needed, where the pulses are targeted to specific areas of muscle tissue on or over the patient's heart. For example, because of the flexible, deformable, and/or bendable aspects associated with the devices and systems set forth herein, a device can be manipulated upon insertion (e.g., before, during, or after insertion) into a patient's body to provide a certain or specific shape, position, arrangement, and/or configuration relative to the patient's heart. This advantageously allows the device to adapt to the size, shape, curvature, and/or contour(s) of the patient's heart. Once the device is provided in a desired shape, position, or configuration, it can advantageously become anchored or locked relative to the patient's heart, either temporarily or permanently.

As used herein, the terms "temporary" and "temporarily" refer to a device or system that is used for a limited amount of time. For example, a temporary device or system refers to those that are removed from the patient's body after a period of time. The period of time can range from about one hour to about fourteen days, including any and all subranges subsumed therein.

As used herein, the terms "permanent" and "permanently" refer to a device or system that is used for a longer amount of time, possibly until a time at which the patient expires. For example, a permanent device or system refers to those that are retained in the patient's body for a period of time ranging from greater than fourteen days to about twenty years, including any and all subranges subsumed therein.

All ranges disclosed herein are understood as encompassing any and all subranges subsumed therein. For example, a stated range of "1.0 to 10.0" is understood as including any and all subranges beginning with a minimum value of 1.0 or more and ending with a maximum value of 10.0 or less, e.g., 1.0 to 5.3, or 4.7 to 10.0, or 3.6 to 7.9.

In addition, all ranges disclosed herein are understood as including the end points of the range, unless expressly stated otherwise. For example, ranges of "between 5 and 10", "about 5 to 10", "5 to 10", or "5-10" are understood as including the recited end points 5 and 10.

Additionally, in any disclosed embodiment, the terms "substantially," "approximately," and "about" may be substituted with "within [a percentage] of" what is specified, where the percentage includes 0.1, 0.5, 1, 5, and 10 percent.

The terms "a" and "an" are defined as "one or more" unless this disclosure explicitly requires otherwise. The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a composition or other object that "comprises," "has," "includes" or "contains" one or more elements possesses those one or more elements, but is not limited to possessing only those elements. Likewise, a method that "comprises," "has," "includes" or "contains" one or more steps possesses those one or more steps, but is not limited to possessing only those one or more steps.

Moreover, any embodiment of any of the compositions, structures, and methods described herein can consist of, or consist essentially of—rather than comprise/include/contain/have—any of the described steps, elements, and/or features. Thus, in any of the claims, the term "consisting of" or "consisting essentially of" can be substituted for any of the open-ended linking verbs recited above, in order to change the scope of a given claim from what it would otherwise be using the open-ended linking verb.

The devices, systems, and methods of treating cardiac arrhythmias described herein are not limited to the specific embodiments presented in the detailed description, examples, and/or figures. It should be recognized that the exemplary embodiments herein are merely illustrative of the principles of the present invention. Numerous modifications and adaptations will be readily apparent to those of skill in the art without departing from the scope of the invention.

I. Devices for Treating Cardiac Arrhythmias

In one aspect, devices for treating cardiac arrhythmias are disclosed herein. Such devices can comprise, consist, or consist essentially of a support member, a plurality of pacing electrodes, and at least one defibrillating electrode. The support member can comprise a first end and second end, and in some cases, a first pacing electrode is disposed proximate the first end of the support member and a second pacing electrode is disposed proximate the second end of the support member. The defibrillating electrode can be disposed between the first pacing electrode and the second pacing electrode.

The devices, or portions thereof, are movable (or configured to move), flexible, bendable, positionable, configurable, expandable, collapsible, deformable, etc., either permanently or temporarily, such that any given device, or portion(s) thereof, can be provided in any one of a plurality of different shapes, sizes, positions, and/or configurations relative to a patient's heart. In some embodiments, the size, shape, position, and/or configuration of devices described herein can advantageously be customized for conforming to differently sized and/or shaped hearts, for example, and without limitation, for conforming to male hearts, female hearts, and children's hearts.

In further aspects, the devices described herein can advantageously conform to the individual curvature, topography, and/or contour(s) of a respective patient's heart for delivering one or more electrical pulses that are precisely targeted to specific tissue in the cardiac wall, such as tissue in the pericardium, myocardium, and endocardium. The decreased distance between the device and the patient's cardiac wall and/or the improved location of the device relative to the patient's heart and/or heart tissue can more effectively regulate the patient's heart beat for treating arrhythmia via application of electrical pulses to the specific, targeted areas of the heart for precisely stimulating specific portions of the heart.

Turning now to specific components of the devices for treating cardiac arrhythmias, such devices can comprise a main body member, also referred to as a support member, and a plurality of electrical signal carriers disposed on or over portions of the support member. Exemplary signal carriers can comprise, include, or consist of, for example, and without limitation, electrically conductive wires, leads, traces, pads, or electrodes. The plurality of electrical signal carriers can be supported by (e.g., on, over, or in) the support member, and in some embodiments, the electrical signal carriers are located over the full or partial length, width, circumference, and/or surface area of the support member. In other aspects, at least some of the plurality of electrical signal carriers can be disposed within a hollow portion or lumen of the support member for routing electrical current to electrical components disposed along the length, width, and/or area of the support member. Any number of signal carriers can be provided per device, and in some embodiments, the signal carriers comprise at least one or more pacing electrodes and at least one or more defibrillating electrodes, each of which is configured to electrically stimulate the heart, or a portion of the heart. In some embodiments, the one or more pacing electrodes can be configured to detect or receive electrical signals in addition to transmitting electrical signals, thereby forming mapping electrodes for mapping conductive heart tissue during a mapping procedure.

The support member can comprise or be formed as a single, unitary support member or a segmented support member formed from a plurality of interconnected segments or portions. Where a unitary support member is provided, it can comprise a flexible or deformable body of material whereby the support member can be formed into any one of a plurality of different two-dimensional shapes from a plan view, including linear and non-linear two-dimensional shapes. For example and in some embodiments, the support member can comprise a deformable material that is bendable from a substantially linear shape (i.e., a line) into a non-linear shape (e.g., a curved line, a zigzag, an angled line, a freeform line, etc.), a circle, a quadrilateral, a helix, an arc, a symmetric shape, an asymmetric shape, or any other shape that is not inconsistent with the objectives of the present disclosure.

The support member can comprise a first, proximal end being disposed proximate to a user (e.g., a surgeon, physician, nurse, etc.), a second, distal end being disposed distally from the user, and a central portion disposed between the first and second ends. The support member can be bendable such that the first and second ends are disposed directly adjacent each other (e.g., in a U-shape, a V-shape, etc.) or disposed a distance away from each other as defined by the non-linear shape of the support member. Notably, a plurality of electrodes can be disposed on or over the unitary flexible or deformable support member and be positioned proximate to specific areas of the heart for mapping and/or selectively stimulating the heart tissue, for example, via pacing or defibrillating as needed, during mapping, pacing and/or defibrillating procedures.

In further embodiments, the devices for treating cardiac arrhythmias described herein can comprise a segmented support member over which one or more pacing/mapping and/or defibrillating electrodes are disposed. The segmented support member can comprise a plurality of discrete, individual segments or portions that can be connected to each other. For example, and in some cases, the pluralities of segments or portions are connected to each other in an end-to-end arrangement. In some embodiments, each individual segment is movable with respect to at least one other individual segment. For example, the segments may be movable via one or more flexible joints that are disposed between adjacent segments. Once positioned in a desired configuration, and in certain embodiments, the segments may then be optionally locked relative to each other during the mapping, pacing and/or defibrillating procedures In an exemplary embodiment, the support member can comprise a first end, a second end opposing the first end, and a center portion disposed between the first and second ends. At least a first joint can connect the first end to the central portion and at least a second joint can connect the second end to the central portion. A device having a support member with three segments (i.e., a first end, second end, center portion) is described herein for exemplary purposes only, as it is recognized that devices having support members with more than three segments or less than three segments can also be provided.

In certain embodiments, the devices described herein comprise a support member having at least two or more segments, where each segment is movable relative to at least one other segment via a flexible joint. Where used, the flexible joint can comprise an area of flexible material (e.g., a metal joint, a plastic joint, etc.), a biasing member (e.g., a spring, a stop, etc.), a hinge, a ball and socket joint, or any other type of joint or connector that is not inconsistent with the objectives of the present disclosure. Where used, the flexible joints can be permanently flexed, temporarily flexed, and/or locked into a desired position such that individual segments can be locked or secured in a desired position, angle, or location with respect to each other and the heart. In an exemplary embodiment, the joint can be permanently flexed where the joint comprises a biasing member or shape-memory alloy.

Further, and in some embodiments, the central portion of the support member defines a longitudinal axis. At least one portion of the support member can bend or flex relative to the longitudinal axis. For example, the first end, the second end, and/or each of the first and second ends can flex, move, deform, or bend relative to the longitudinal axis. Additionally, one or more individual segments of a segmented support member can be flexed, moved, or bent relative to the longitudinal axis. As electrodes are disposed over various portions and/or segments of the support member, flexing or bending one or more portions of the support member can advantageously position one or more of the electrodes more closely adjacent to target tissue in the heart. "Target tissue" refers to heart tissue that is to be mapped and/or electrically stimulated via mapping, pacing, and/or defibrillating electrodes. The target tissue may be disposed in one or more portions or layers of the heart, including any of the endocardium, myocardium, pericardium, or combinations thereof.

Still referring to the support member and in some embodiments, the support member is fully or partially positionable between a linear configuration and at least one non-linear configuration. For example, and in some embodiments, the first end of the support member can be flexed or bent to contour a first region of the heart and the second end of the support member can be flexed or bent to contour a second region of the heart. In some embodiments, the first end is positioned adjacent a first chamber and/or ventricles of the heart for stimulating multiple portions of the heart, as needed. In many cases, it may be necessary to pace both the left and right sides of the heart to mimic the natural pacing of the heart and coordinate the function between the atria and ventricles. The devices and systems herein can advantageously provide permanent and/or temporary pacing of various locations on a heart, including both sides of the heart, in a minimally invasive manner.

The devices for treating cardiac arrhythmias can further comprise one or more electrical signal carriers disposed on, over, and/or within portions of the support member. The electrical signal carriers refer to electrodes, leads, traces, pads, and/or wires used to transmit, carry, route, and/or receive electrical current during mapping, pacing, and/or defibrillating procedures. For example, and in some embodiments, the electrical leads can be disposed internally within a hollow region of the support member for internally carrying electrical signal or current to one or more external electrodes, such as the plurality of mapping/pacing and defibrillating electrodes. The support member can be entirely hollow (e.g., as a lumen) or at least partially hollow for housing a plurality of sheathed electrical wires or leads. The sheathed wires or leads can supply electrically current or power to the mapping, pacing, and/or defibrillating electrodes.

Further, and in some embodiments, a plurality of electrical signal carriers in the form of electrodes can be selectively energized to map, pace, and/or defibrillate target sites on the heart, as needed. Such electrodes can comprise or be formed as traces or pads disposed on or over a circuit board, traces or pads disposed on or over the support member, electrically conductive coils disposed on or over the support member, or the electrodes may be formed by exposing some portions of the electrical signal carriers to map, pace, or defibrillate the heart. For example and in certain aspects, an insulating cover or sheath surrounding a respective signal carrying lead or wire can be stripped or otherwise removed to expose a portion of the carrier to form a mapping or pacing electrode. In certain embodiments, the mapping or pacing electrodes are configured to sense or detect electrical current in conductive heart tissue for mapping and/or pacing the damaged tissue. Where damaged heart tissue is detected by mapping electrodes, the electrodes can then be configured as pacing electrodes to transmit electrical current to a target site for stimulating and contracting portions of the heart thus treating a cardiac arrhythmia. Notably, the defective tissue can be mapped as the heart is beating during a minimally invasive technique.

Furthermore, in some embodiments, the pacing and defibrillating electrodes can be configured to selectively and independently transmit the electrical impulses for pacing and defibrillating the heart, respectively. In other words, although multiple pacing electrodes can be provided, less than all of the pacing electrodes can be energized to provide the pacing impulses based on the locations determined to require electrical stimulation. Moreover, where one or more defibrillating electrodes are present, one or none of the defibrillating electrodes may be selected for providing the defibrillating energy, and energizing the one or more defibrillating electrodes may occur with or without energizing of one or more of the pacing electrodes. Stated differently, the mapping/pacing and defibrillating electrodes are independently operable.

Additionally, the pacing electrodes and/or the defibrillating electrodes may electrically communicate with and/or be controlled by a pulse generator. In some embodiments, the pulse generator is disposed outside of the patient's body. In further embodiments, the pulse generator is disposed within the patient's body, for example, below the subcutaneous fat of the chest wall or above the muscles and bones of the patient's chest. The pacing and/or mapping electrodes can be configured in pairs and the defibrillating electrode can comprise at least one coil that is wrapped around portions of the support member. In certain embodiments, the pulse generator can comprise a power source, a sensor, and/or a controller that collectively sense or detect heart-related data and control the transmission of electrical pulses communicated to the electrodes in response to receiving/sensing heart-related data that indicates that electrical pulses are needed to stimulate the heart.

Notably, the devices for treating cardiac arrhythmias described herein can be attached to a portion of the heart, including, for example, the pericardium or epicardium. In some embodiments, devices herein can comprise an attachment member disposed at the first and/or the second end of the support member for affixing the device to a portion of the heart, as desired.

Additionally, the devices described herein can further comprise a plurality of anchor members that are disposed on, over, or within portions of the support member. The plurality of anchor members can be extendable and retractable relative to a surface of the support member and, in an extended position, engage a portion of the heart to inhibit movement of the device in a distal and/or proximal direction. The plurality of anchor members can be acutely or obtusely angled relative to the surface of the support member for securing the device in a desired shape, location, or position relative to the heart.

In some embodiments, a first plurality of distal anchor members can be disposed at the first end of the support member to inhibit movement of the device in the distal direction and a second plurality of proximal anchor members can be disposed at the second end of the support member to inhibit movement of the device in the proximal direction. The device can optionally comprise a plurality of anchor members disposed at each of the first end, the second end, and the central portion of the support member for inhibiting movement of the device relative to the heart.

Further, the support member, or portions thereof, can be rotatable, bendable, flexible, and/or deformable relative to a longitudinal axis defined by one portion of the support member and then secured in place relative to the heart for conforming to the contour(s) and/or topology of the heart for mapping, pacing, and/or defibrillating the heart to treat cardiac arrhythmias.

The devices described herein can electrically stimulate a target site in a patient's heart to treat abnormalities in any one of several layers in the patient's heart. It will be appreciated that the support member is movable to any one of a linear or non-linear two-dimensional shape or configuration for positioning the mapping, pacing, and/or defibrillating electrodes proximate target portions of the heart to treat cardiac arrhythmias. At least one defibrillating electrode can be disposed on or over the same unitary or segmented support member as the one or more mapping and/or pacing electrodes, and in some aspects, between the one or more mapping and/or pacing electrodes.

Persons skilled in the art will appreciate that the device, and/or portions thereof as described hereinabove, may be separated, combined, and/or integrated into one or more components, as desired, for accomplishing the mapping, pacing, and/or defibrillating procedures to treat cardiac arrhythmias described herein.

II. Systems for Treating Cardiac Arrhythmias

In a further aspect, systems for treating cardiac arrhythmias are provided. In some embodiments, such systems can comprise any device as described hereinabove in Section I. The systems described herein can further comprise a data recorder and/or an optional computer for monitoring and/or regulating electrical energy transmitted to one or more portions of the heart.

In some embodiments, a data recorder can comprise a sensor or detector configured to detect heart-related data. The data recorder may be integrated with a portion of the pulse generator described above, or it may be a separate device disposed outside of the patient's body. Any location or arrangement of the data-recorder that is not inconsistent with the objections of the instant disclosure is contemplated.

The computer may be configured to read, collect, store, and/or monitor the heart-related data. Such heart-related data can comprise, without limitation, electrical data relating to the heart, heart beat data, timing data, or other data indicative of the functioning of the heart not inconsistent with the instant disclosure. The computer can comprise or be formed as a local, micro-computer that is integrated within a portion of the pulse generator as described above, for reading the data and instructing a controller to generate a desired pulse at the pulse generator. In other aspects, the computer is a remote machine for obtaining data from outside of the patient's body whereby a physician or doctor can monitor the patient's heart-related data obtained by the data recorder.

In some embodiments, the systems for treating cardiac arrhythmias are temporary systems. In other embodiments, the systems for treating cardiac arrhythmias are permanent systems. Temporary systems can be removed from a patient's body after a predetermined period of time. The predetermined period of time can range from about one hour to about fourteen days. In some embodiments, a temporary system and/or a portion thereof (e.g., the device) is removed after at least one hour, at least six hours, at least twelve hours, at least twenty-four hours, at least two days, at least five days, at least seven days, at least ten days, or at least ten days.

In contrast, the permanent devices and/or systems can be retained within the patient's body for a period of time ranging from greater than fourteen days to about twenty years. A permanent system and/or a portion thereof (e.g., the device, pulse generator, etc.) can be retained within a patient's body for at least 21 days or more, at least 3 months or more, at least 6 months or more, at least one year or more, at least five years or more, at least ten years or more, at least fifteen years or more, or at least twenty years. Such systems can comprise or include a battery that can be replaced periodically, as needed.

In an exemplary embodiment, a temporary system can comprise a device that is at least partially disposed within the patient's body and at least partially disposed outside of the patient's body. For example, and in some embodiments, the support member and electrodes can be disposed within the patient's body, while portions of the electrical leads, wires, and/or pulse generator (e.g., power supply) can be disposed outside of the patient's body. The pulse generator can be activated by electrical power to generate and transmit controlled electrical pulses that are routed to one or more electrodes in response to data collected by the data recorder and/or computer. The controlled electrical pulses can be delivered to the target tissue via the specifically configured electrodes of the device.

In another exemplary embodiment, a permanent system can comprise a device that is fully disposed within the patient's body. For example and in some embodiments, the support member, electrodes, power supply (e.g., pulse generator), and/or data recorder can each be disposed within the patient's body. The data recorder can collect data from a point that is inside or outside of the patient's body, and send the data to a computer. The computer can instruct the pulse generator to transmit electrical energy in the form of pulses to the heart, as needed, in response to detecting a cardiac arrhythmia and/or cardiac arrest.

Moreover, the data recorder can collect and/or store heart-related data obtained via the devices and/or electrodes disposed on the devices as described herein. Such data may include, for example, the strength of the electrical impulses carried by the conductive tissue of the heart, the timing of electrical impulses carried by the conductive tissue of the heart, the timing of and/or between contractions of the heart, and/or any other data relating to the timing, synchronization, and/or strength of contractions within the heart. In some embodiments, the heart-related data collected by the data recorder can be transmitted, collected, and/or read through the patient's skin.

In further embodiments, the computer and/or a computing program can download the heart-related data collected by the data recorder via a wireless connection, a wired connection, or the Internet. In some embodiments, the data recorder is disposed in the computer; in other embodiments the data recorder and computer are separate computing entities.

Persons skilled in the art will appreciate that the device, and/or portions thereof as described hereinabove may be separated, combined, and/or integrated into one or more device or system components, as desired, to accomplish the recording, computing, and controlling of electrodes to treat cardiac arrhythmias as described herein.

III. Methods of Treating Patients

In yet a further aspect, methods for treating cardiac arrhythmias are provided. Methods of treating a patient can comprise, for example, providing any of the devices as described hereinabove in Section I.

A method of treating a patient can further comprise, for example, disposing any of the devices described in Section I above adjacent a heart of the patient. Disposing a device adjacent the heart of the patient can comprise making an incision in a thoracic area of the patient's body an inserting the device into the incision. In some embodiments, inserting the device into the incision comprises inserting the entire device into the incision such that no portion of the device is disposed outside of the patient's body. Alternatively, and in other embodiments, inserting the device into the incision comprises inserting only a portion of device into the incision such that at least some other portion of the device remains outside of the patient's body.

In some embodiments, disposing the device adjacent the heart of the patient comprises flexing the first end of the support member relative to the longitudinal axis defined by the central portion of the support member for positioning the first pacing electrode proximate a first region of the heart and flexing the second end of the support member relative to the longitudinal axis for positioning the second pacing electrode proximate a second region of the heart.

Additionally, the methods described herein can include attaching the first end of the support member to a first region of the heart via an attachment member and optionally anchoring the device in a position relative to the heart using one or more anchoring members that extend from a surface of the support member.

Methods of treating a patient can optionally comprise mapping one or more areas of the heart via one or more mapping electrodes during a mapping procedure to locate a source of a cardiac arrhythmia. Other methods include energizing one or more of the plurality of pacing electrodes to transmit electrical energy to the heart during a pacing operation to treat a cardiac arrhythmia. The method may further and optionally comprise energizing the defibrillating electrode to transmit electrical energy to the heart during a defibrillating operation to treat a cardiac arrhythmia.

In some embodiments, an optional antimicrobial coating, layer, material, cuff, sleeve, or envelope is disposed around portions of the device for minimizing the potential for infection during treatment with devices or systems described herein.

The methods of treating a patient as described herein can further comprise removing the device or system from the patient's body after a predetermined period of time, where the predetermined period of time ranges from about one hour to about one year. In contrast, the device and/or system may optionally be retained within the patient's body for a period of time ranging from about one year to about twenty years.

The methods described herein can further comprise coupling the device to a data recorder that records heart-related data. The heart-related data collected via the data recorder can be read through the patient's skin and/or be downloaded to a computer via a wireless connection (e.g., wireless antennae), a wired connection, or the Internet.

Some embodiments described herein are further illustrated in the following non-limiting examples.

Example 1

Devices for Treating Cardiac Arrhythmias

Figure 1:
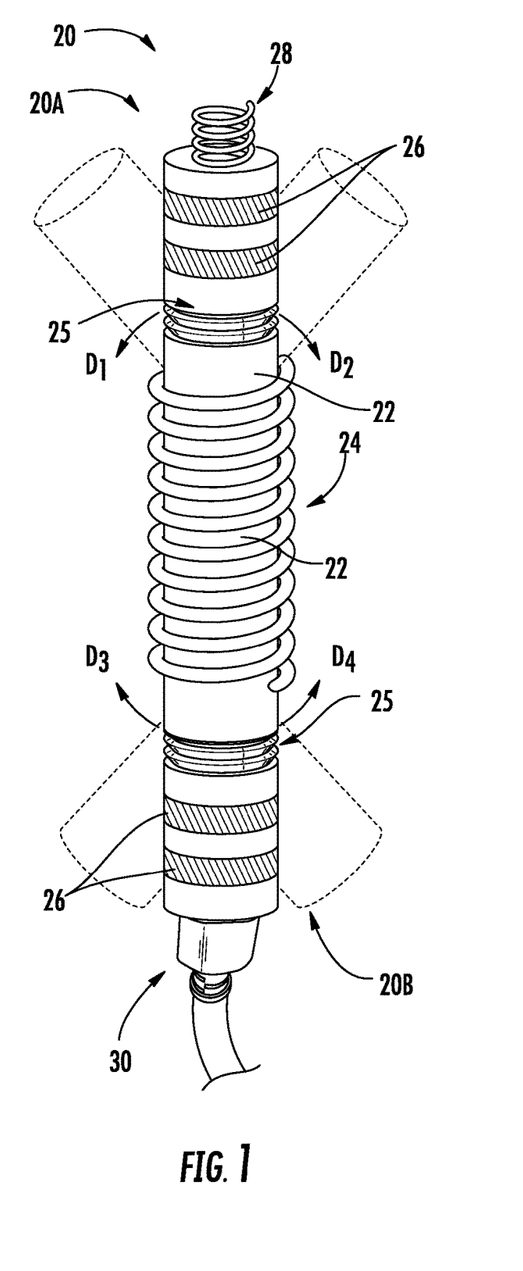
FIG. 1 illustrates an exemplary device for treating cardiac arrhythmias according to a first embodiment of the subject matter described herein.
Figure 2:
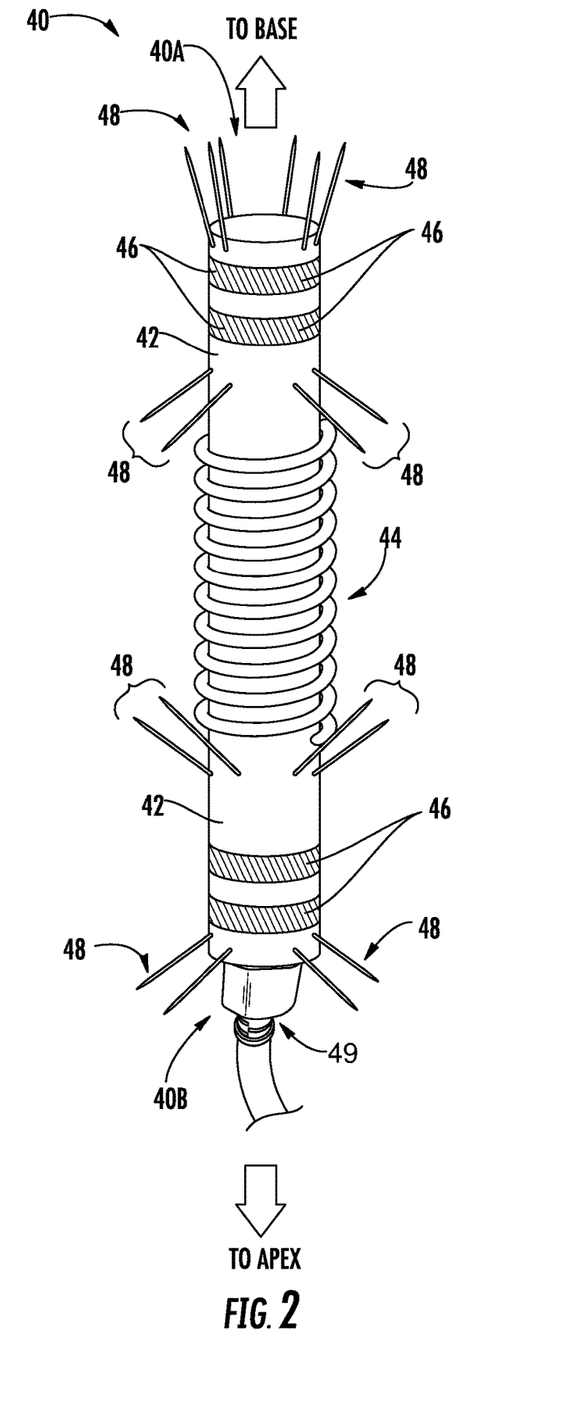
FIG. 2 illustrates an exemplary device for treating cardiac arrhythmias according to a further embodiment of the subject matter described herein.

Devices for treating cardiac arrhythmias, generally referred to as 20 and 40, are illustrated in FIGS. 1 and 2, respectively. Referring to FIG. 1, such a device 20 can comprise a support member 22 having a first end 20A, also referred to herein as a distal end, and a second end 20B, also referred to herein as a proximal end. The proximal end 20B can closer to the user (e.g., a surgeon, physician, nurse, etc.) than the distal end 20A during placement of the device. Each respective end 20A, 20B of the device 20 can comprise one or more electrodes 26, or pairs of electrodes, being configured to map and/or pacing the heart during mapping or pacing procedures.

At least one defibrillating electrode 24 is disposed between first and second ends 20A, 20B and/or between respective electrodes 26 at the first and second ends 20A, 20B. More than one defibrillating electrode 24 may be provided per device 20, where desired. In some embodiments, the defibrillating electrode 24 comprises a coil that is disposed on, over, and/or around portions of the support member 22.

In certain embodiments, the defibrillating electrode 24 is disposed over a central body portion of the support member, which is connected to opposing 20A, 20B of the support member via flexible regions or joints 25. These flexible joints 25 permit the device to be flexed, bent, or contoured over a patients' heart, for example, the pericardium or epicardium of the heart.

For example, as FIG. 1 illustrates, the terminal end portions of the device 20 can be flexed or moved in at least a first direction D1, a second direction D2, a third direction D3, and a fourth direction D4. Movement of the device 20 in any desired direction not inconsistent with the instant disclosure is contemplated. The flexible joints 25 are optionally lockable, so that the desired shape or position of the device 20 can be retained once the device is located next to a heart and/or heart tissue.

The device 20 can further comprise at least one anchoring or attachment member 28 disposed proximate one or both ends 20A, 20B. In the exemplary embodiment illustrated in FIG. 1, the attachment member 28 is depicted as a helical screw. Any other type, size, shape, etc., of attachment member that is not inconsistent with the objectives of the present disclosure may be provided at one or both ends of the device 20. For example, the attachment member 28 can comprise a screw, pin, hook, clip, piercing member, etc. In some embodiments, the attachment member 28 is disposed at the distal end 20A of the device for "active" fixation of the device at a desired site, such as the pericardium or a surface thereof. In other embodiments, the attachment member 28 is disposed at the proximal end 20B of the device. The proximal end 20B of the device 20 can comprise plug 30 or bundle comprised of electrical wires configured to carry electrical current to the electrodes 26 and/or coil 24 for use in mapping/pacing and/or defibrillating procedures.

FIG. 2 illustrates aspects of a further device, generally designated 40, for treating cardiac arrhythmias. The device 40 comprises a support member 42 having a first end 40A, also referred to herein as a distal end, and a second end 40B, also referred to herein as a proximal end. One or more electrodes 46 are disposed at each end of the device 40. The electrodes 46 are configured to map and/or pace the heart during mapping and/or pacing procedures.

At least one defibrillating electrode 44 is also disposed on device 40. The defibrillating electrode 44 can be disposed over the support member 42 between the first and second ends 40A, 40B and/or between electrodes 46 at the first and second ends 40A, 40B of the device 40. In certain embodiments, the defibrillating electrode 44 is a defibrillating coil that is disposed on, over, and/or around portions of the support member 42.

The device 40 in FIG. 2 is an exemplary embodiment of a "passive" fixation system. The device 40 comprises a plurality of extendible and retractable anchor members 48 that prevent or hinder movement of the device 40 in a distal/proximal direction once it is placed in a desired location relative to the patient's heart. The anchor members 48 may be obtusely or acutely angled relative to a surface of the device 40. In some embodiments, distal extensions extending from the distal end 40A are substantially "forward facing" relative to the defibrillating electrode 44 so that they prevent or hinder the device 40 from being pushed farther in the distal direction, toward the base of the heart (see the top arrow in FIG. 2). Proximal extensions extending from the proximal end 40B are substantially "rear facing" relative to the defibrillating electrode 44 so that they prevent or hinder the device from being pulled farther "out" in a proximal direction, toward the apex of the heart (see the lower arrow in FIG. 2).

In some embodiments, the distal end 40A of the support member 42 is a free end of the tube the proximal end 40B end of the support member 42 is attached to a pulse generator.

For example, the proximal end 40B of the device 40 can comprise plug 49 or bundle comprised of electrical wires that carries electrical current to the electrodes 46 and/or coil 44 for use in mapping/pacing and/or defibrillating procedures.

It should be recognized that the instant figures are merely illustrative of the principles of the present invention. Numerous modifications and adaptations thereof will be readily apparent to those skilled in the art without departing from the spirit and scope of the invention.

Example 2

Systems for Treating Cardiac Arrhythmias

Figure 3:
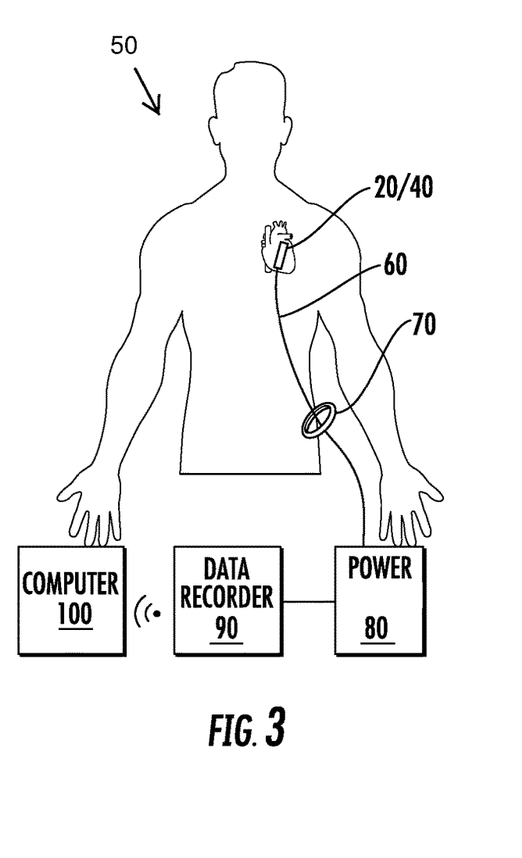
FIG. 3 illustrates an exemplary system for treating cardiac arrhythmias according to a first embodiment of the subject matter described herein.
Figure 4:
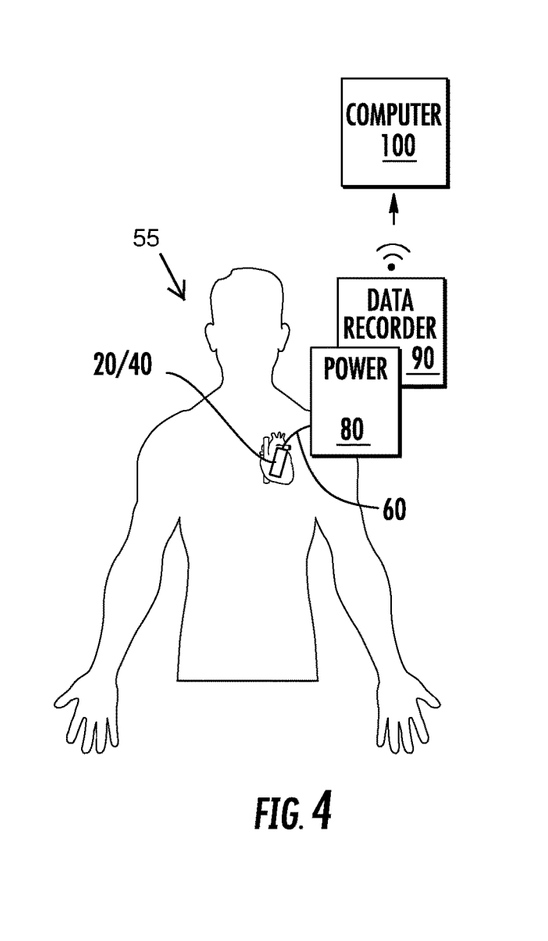
FIG. 4 illustrates an exemplary system for treating cardiac arrhythmias according to a further embodiment of the subject matter described herein.

Systems for treating cardiac arrhythmias are provided in FIGS. 3 and 4. The systems and devices depicted in FIGS. 3 and 4 can be "temporary" or "permanent" systems and devices.

FIGS. 3 and 4 illustrate respective systems 50 and 55 that comprise or consist of a device for treating cardiac arrhythmias 20 or 40, as described in Example 1 above. FIG. 3 illustrates a wired system 50, which may be suitable for temporary use whereas FIG. 4 depicts a wireless system 55 and device, which may be suitable for a permanent use. The wired and wireless systems 50 and 55 may be used for either temporary or permanent applications, as desired.

Referring to FIG. 3 and in certain embodiments, a temporary system 50 can be formed from lighter (less dense, less heavy) materials and may be connected to an external power source 80 (e.g., a pulse generator) through the skin using an electrical signal carrying lead 60. An antimicrobial cuff 70 can optionally be deployed over or around the lead 60 and beneath the surface of the skin to prevent microbes or other foreign matter from entering the patient's body via the lead. The lead 60, or other type of wired interface or connector, can connect the device 20/40 to a power source 80 and a data recorder 90. The data recorder 90 can transmit recorded heart information to a computer 100, either via a wired connection or a wireless connection using, for example, a wireless interface or antennae. The information is used to perform, monitor, or assess mapping, pacing, and/or defibrillating procedures.

A permanent version of the system may be formed from heavier weighted materials and/or can be connected to an internal power source 80 device through a subcutaneous lead 60. An internal power supply 80 can be smaller than an external power supply. An internal power supply can also be configured to be replaced every 30 days, every 90 days, or at some other time interval. Further, as FIG. 4 illustrates and in some embodiments, the power supply 80 can be integrated with the data recorder 90. The integrated devices may be disposed inside or outside of the patient's body.

In certain embodiments, the data recorder 90 and power supply 80 can be housed together or form part of a single accessory "box" for use with the device 20/40. If desired, heart-related data obtained at the data recorder 90 can be read through the patient's skin. Alternatively, the heart-related data can be received and downloaded at computer 100. The heart-related data can be downloaded via a wired or wireless Internet connection.

Various embodiments of the present invention have been described in fulfillment of the various objectives of the invention. It should be recognized that these embodiments are merely illustrative of the principles of the present invention. Numerous modifications and adaptations thereof will be readily apparent to those skilled in the art without departing from the spirit and scope of the invention.

The invention claimed is:

1. A device for treating cardiac arrhythmias, the device comprising:
   a physically segmented support member comprising a central portion, a first end body and a second end body opposing the first end body, each end body of the physically segmented support member being separated from the central portion by a joint and configured to be independently flexible or bendable;
   a plurality of pacing electrodes comprising at least a first pacing electrode being disposed proximate the first end body of the physically segmented support member and at least a second pacing electrode being disposed proximate the second end body of the physically segmented support member;
   at least one defibrillating electrode disposed between the first pacing electrode and the second pacing electrode;
   a plurality of electrical connectors that electrically communicate to one or more of the plurality of pacing electrodes and/or the defibrillating electrode, the plurality of electrical connectors being positioned within a portion of the physically segmented support member; and
   an attachment member for affixing the device to a portion of a heart, the attachment member being disposed at the first and/or the second end body of the physically segmented support member, wherein
   the central portion defines a longitudinal axis, the central portion being disposed between the first end body and the second end body, wherein at least one of the first end body and the second end body is configured to independently flex or bend relative to the longitudinal axis via the joint, wherein the physically segmented support member comprises at least a first joint connecting the first end body to the central portion and at least a second joint connecting the second end body to the central portion, and wherein the physically segmented support member is configured to position one or more of the plurality of pacing electrodes and/or the defibrillating electrode adjacent target tissue.

2. The device of claim 1, wherein the physically segmented support member is positionable in a linear configuration and a non-linear configuration, such that the first end body of the physically segmented support member contours a first region of a heart and the second end body of the physically segmented support member contours a second region of the heart.

3. The device of claim 1, further comprising a plurality of anchor members, wherein the plurality of anchor members are extendable and retractable relative to a surface of the physically segmented support member and are operable, in an extended position, to engage a portion of a heart to inhibit movement of the device in a distal and/or proximal direction.

4. The device of claim 3, wherein the anchor members are acutely or obtusely angled relative to the surface of the physically segmented support member,
   wherein a plurality of distal anchor members are disposed at the first end body of the physically segmented support member to inhibit movement of the device in the distal direction, and
   wherein a plurality of proximal anchor members are disposed at the second end body of the physically segmented support member to inhibit movement of the device in the proximal direction.

5. The device of claim 1, further comprising a plurality of anchor members disposed at each of the first end body, the second end body, and the central portion of the physically segmented support member that inhibit movement of the device relative to a heart.

6. The device of claim 1, wherein:
   the physically segmented support member comprises a hollow tube;
   the first end body of the physically segmented support member is a free end of the tube; and
   the second end body of the physically segmented support member is attached to a pulse generator.

7. The device of claim 1, wherein the device is configured to be attached to a pericardium or a surface of the pericardium.

8. A method of treating a patient, the method comprising:
   providing the device of claim 1; and
   disposing the device adjacent a heart of a patient.

9. The method of claim 8, wherein disposing the device adjacent the heart of the patient comprises:
   making an incision in a thoracic area of a body of the patient; and
   inserting the device into the incision.

10. The method of claim 9, wherein inserting the device into the incision comprises inserting the entire device into the incision such that no portion of the device is disposed outside of the body of the patient.

11. The method of claim 9, wherein inserting the device into the incision comprises inserting only a portion of device into the incision such that at least some portion of the device remains outside of the body of the patient.

12. The method of claim 8, wherein disposing the device adjacent the heart of the patient further comprises:
   flexing the first end body of the physically segmented support member relative to the longitudinal axis defined by the central portion of the physically segmented support member for positioning the first pacing electrode proximate a first region of the heart; and
   flexing the second end body of the physically segmented support member relative to the longitudinal axis for positioning the second pacing electrode proximate a second region of the heart.

13. The method of claim 8, further comprising attaching the first end of the physically segmented support member to a first region of the heart via the attachment member.

14. The method of claim 8, further comprising anchoring the device in a first position relative to the heart using one or more anchoring members extending from a surface of the device.

15. The method of claim 8, further comprising:
   energizing one or more of the plurality of pacing electrodes to transmit electrical energy to the heart during a pacing operation; or
   energizing the defibrillating electrode to transmit electrical energy to the heart during a defibrillating operation.

16. The method of claim 8, further comprising removing the device from the body of the patient after a predetermined period of time, the predetermined period of time ranging from one hour to fourteen days or from greater than fourteen days to twenty years.

17. The method of claim 8, further comprising:
   coupling the device to a data recorder that records heart-related data; and
   reading the heart-related data collected via the data recorder through the skin of the patient.

18. The method of claim 8, wherein the device is attached to the patient's pericardium or a surface of the pericardium.

\* \* \* \* \*